United States Patent [19]

Paau

[11] Patent Number: 4,875,921

[45] Date of Patent: Oct. 24, 1989

[54] BACTERIAL AGRICULTURAL INOCULANTS

[75] Inventor: Alan Paau, Middleton, Wis.

[73] Assignee: Agracetus Corporation, Middleton, Wis.

[21] Appl. No.: 67,428

[22] Filed: Jun. 26, 1987

Related U.S. Application Data

[63] Continuation of Ser. No. 727,029, Apr. 25, 1985, abandoned.

[51] Int. Cl.$^4$ .............................................. C05F 11/08
[52] U.S. Cl. .......................................... 71/7; 47/57.6; 47/DIG. 9; 47/DIG. 10; 435/176; 435/260
[58] Field of Search ........................ 71/6, 7; 47/57.6; 435/174, 176, 260

[56] References Cited

U.S. PATENT DOCUMENTS

| | | | |
|---|---|---|---|
| 2,726,948 | 12/1955 | Erickson | 71/7 |
| 2,932,128 | 4/1960 | Porter et al. | 47/58 |
| 3,034,968 | 5/1962 | Johnston | 34/9 |
| 3,054,219 | 9/1962 | Porter et al. | 71/7 |
| 3,168,796 | 2/1965 | Scott et al. | 71/7 X |
| 3,616,236 | 10/1971 | Dalin | 435/172.1 |
| 3,703,404 | 11/1972 | Kirk | 428/404 |
| 4,149,869 | 4/1979 | Lloyd | 71/7 |
| 4,258,074 | 3/1981 | Grimm et al. | 47/DIG. 9 |
| 4,421,544 | 12/1983 | Jones et al. | 71/7 |
| 4,434,231 | 2/1984 | Jung | 71/7 X |
| 4,465,017 | 8/1984 | Simmons | 47/57.6 |
| 4,504,582 | 3/1985 | Swann | 435/108 |

FOREIGN PATENT DOCUMENTS

| | | | |
|---|---|---|---|
| 0063438 | 10/1982 | European Pat. Off. | 435/260 |
| 192342 | 8/1986 | European Pat. Off. | |
| 2519022 | 7/1983 | France | 435/260 |

OTHER PUBLICATIONS

Chao et al., Applied & Environmental Microbiology, 47:1, pp. 94–97, 1984.
Davidson et al., Applied & Environmental Microbiology, 35:1, pp. 94–96, (1978).
Dye, Journal of Applied Bacteriology, 52, pp. 461–464, (1982).
Redway et al., Cryobiology, 11, pp. 73–79, 1974.
Vincent et al., "Death of Root-Nodule Bacteria on Drying", 1961.

Primary Examiner—Ferris H. Lander
Attorney, Agent, or Firm—Nicholas J. Seay; Philip L. McGarrigle; Albert P. Halluin

[57] ABSTRACT

A method for making an agriculturally useful inoculant of dried, dormant bacteria is described. To make the inoculant, a suspension of Rhizobium or other bacteria is maintained, substantially separated from its culture medium, at a temperature in the range of about 0°–30° C. for varying periods of time under aseptic conditions. The bacterial suspension is then mixed with a porous chemically inert granular carrier such that the weight ratio of carrier to bacteria is in the range of about 0.5 to 1.0. Finally, the bacteria-carrier mixture is air dried for a period of about 2 to 10 days under aseptic conditions.

7 Claims, No Drawings

BACTERIAL AGRICULTURAL INOCULANTS

This application is a continuation, of application Ser. No. 727,029, filed Apr. 25, 1985 and now abandoned.

FIELD OF THE INVENTION

The present invention relates to bacterial agricultural products, including Rhizobium inoculants, and methods for making and preserving such agricultural products.

BACKGROUND OF THE INVENTION

It is well known that leguminous plants under certain conditions "fix nitrogen" directly from the air and convert it to organic nitrogenous compounds, thereby providing nitrogen to the plant for protein synthesis and also enriching the soil around the leguminous plants by leaving nitrogenous nutrients in the soil for later crops. In actual fact, of course, the plants themselves do not fix nitrogen, but the nitrogen fixation occurs in Rhizobium bacteria which exist symbiotically with the legumes in nodules formed in the roots of the plants. Examples of leguminous plants which are capable of symbiotic relationship with Rhizobium bacteria are peas, beans, alfalfa, red clover, white clover, vetch, lupines, and the like.

Other agriculturally important non-leguminous plants, such as grasses and grains, are unable to fix nitrogen directly from the air. Non-Leguminous plants generally depend entirely upon combined nitrogen in the soil, such as nitrates and ammonium salts for nitrogen for protein synthesis. After a series of such crops have been grown on any given field, the combined nitrogen in the soil becomes depleted. Consequently, crop rotation is often practiced, whereby nitrogen-fixing plants are grown in rotation with non-nitrogen-fixing plant to replenish soil nitrogen. Furthermore, some legumes, particularly soybeans, peas, beans and alfalfa, are commercially important as crops themselves, and the growth of these crop plants is greatly facilitated by ample combined nitrogen availablity.

The particular Rhizobium bacteria necessary to a given nitrogen-fixing plant may be universally present in the soil. Different Rhizobium species are adapted to form nodules only in legumes of specific species. Therefore, it is a quite common practice to inoculate the seeds of leguminous plants with an appropriate culture of Rhizobium bacteria. The inoculation can be done by coating the seeds, dusting planted seeds or crops, or by spreading inoculant in the furrows of planted leguminous seeds.

One method of inoculating leguminous seeds is to maintain the Rhizobium bacteria culture in an active living state, by mixing a moist culture of the bacteria with a carrier such as humus or peat. The carrier maintains the bacteria in a moist, living state. However, the shelf life of such live bacterial cultures can be relatively short, because the bacteria die under conditions of storage due to the relative shortage of food and moisture in their environment. An example of a moist type of inoculant mixture is described in U.S. Pat. No. 2,726,948 to Erickson, wherein an active moist bacterial culture is mixed with a mixture of peat, charcoal and limestone, so that water is present to the level of approximately 38% by weight of the whole.

Another method of preparing legume seed inoculants is to convert the bacteria culture to a state of dormancy. One known method used to create dormant bacteria is freeze-drying, as described in U.S. Pat. No. 3,168,796 to Scott, et al. In Scott, Rhizobium bacteria are freeze-dried at temperatures in the range of −35° to −70° C. The dried bacterial cake is then ground and blended with a powdered carrier, which carrier is a non-hydroscopic inert powder less than 40 microns in size. The weight ratio of bacteria to carrier in the Scott patent is in the range of 5 to 400 milligrams bacteria per ounce of carrier. According to the Scott patent, it is critical that water be excluded during the mixing step between bacteria and carrier.

Although freeze-drying Rhizobium bacteria prior to mixing with a carrier usually gives a high initial recovery, the bacteria does not always remain stable for long storage periods. Therefore, it would be advantageous to provide a dry, dormant Rhizobium inoculant which can be easily prepared and which will be stable over fairly long storage times with high yields of viable Rhizobium upon re-exposure to moisture.

Some have suggested that other, non-rhizobium, bacteria may be beneficial to some crop plants. Many terrestrial bacterial species are known and it is quite possible that some may be particularly helpful in the cultivation of field crops because of symbiotic relationships formed between plant and bacteria. In the event such associations are identified, it would become necessary to be able to effectively deliver the bacteria to the field in order to take advantage of this symboisis.

SUMMARY OF THE INVENTION

The present invention is summarized as a method for making a dry agriculturally useful composition containing dormant bacterial culture on an inert granular carrier. A colony of Rhizobium, or other species of bacteria, is cultured in bulk, is separated from the culture medium and maintained at a temperature in the range of about 0° to 30° C. for a time period of about 0 to 96 hours under aseptic conditions. The bacteria is then mixed with a porous, chemically inert granular carrier such that the weight ratio of bacteria to culture is in the range of about 0.5 to 1.5. The bacteria-carrier mixture is then air dried at room temperature for a period of about 2 to 10 days under aseptic conditions.

It is an object of the present invention to provide a method for making an agriculturally useful composition including viable dormant bacteria, either Rhizobium or other useful species.

It is a further object of the present invention to provide a bacterial inoculant in which the bacteria will be dormant and easily handleable, yet in which the bacteria will be stable and viable during extended storage time.

It is a still further object of the present invention to provide a seed coating for legumes which includes a Rhizobium inoculant in which the coating and the seed will be stable during long storage periods.

Other objects, advantages, and features of the present invention will become more apparent from the following detailed description.

DESCRIPTION OF THE PREFERRED EMBODIMENT

The present invention discloses a method for making an agriculturally useful composition including a viable bacterial component, especially useful with Rhizobium bacteria. The bacteria culture itself can be efficiently grown either on a semisolid support such as AMA-agar or in the liquid state (AMA-liquid). After a suitable bulk quantity of the appropriate desired strain of Rhizobium or other bacteria has been cultured, the bacteria are harvested from the culture medium. Suitable Rhizobium species include *R. japonicum*, used with soybeans; *R. trifolii*, used with clovers; *R. meliloti*, used with alfalfa and sweet clovers; *R. leguminosarum*, used with peas and vetches; *R. phascoli*, used with garden beans; and *R. lupini*, used with lupines. Mixtures of the separate species of Rhizobium may also be used. The harvesting method selected depends on the type of culture used. For instance, if a semisolid support such as AMA-agar is used, the bacteria can be harvested by scraping the culture off the top of the agar. If a liquid culture is used, the bacteria can be separated from its culture medium by centrifugation.

Once the Rhizobium bacteria have been substantially separated from the culture medium, the bacteria are maintained at a temperature in the range of about 0° to 30° C. for a period in the range of about 0 to 96 hours under aseptic conditions. Preferably, the bacterial suspension is maintained at a temperature in the range of about 22° to 30° C., i.e. a normal room temperature, for a period in the range of about 3 to 25 hours under aseptic conditions, followed by further maintaining the bacterial suspension at a temperature in the range of about 0° to 15° C. for a period in the range of about 3 to 20 hours under aseptic conditions. The bacteria are maintained as a concentrated liquid suspension during this step. At this stage, after the bulk of the liquid medium has been removed, the bacteria are no longer actively growing. For Rhizobium, the density should be on the order of $10^7$ to $10^{12}$ bacteria per milliliter. The concentrated bacteria suspension should be a dense liquid appearing more like a viscous paste.

The concentrated bacterial suspension is then mixed with a porous, chemically inert granular carrier such that the weight ratio of concentrated bacteria suspension to dry carrier is in the range of about 0.5 to 1.5, preferably about 1.0. Examples of suitable carriers include vermiculite, perlite, and charcoal. If charcoal is used, a saturated saccharide solution, preferably selected from the group consisting of sucrose, lactose, trehalose, sorbitol and adonital, is added to the bacterial suspension prior to the step of maintaining the bacteria at 0° to 30° C. The weight of the saturated saccharide solution added to the bacteria suspension is in a ratio in the range of about 0.5–1.5, preferably about 1.0 by weight. Charcoal carriers are advantageous and may be preferable for some applications because the charcoal may absorb Rhizobium-toxic compounds, such as alkaloids and lignin compounds, which are naturally released by many legume seeds during germination.

Next, the bacteria-carrier mixture is slowly dried, preferably in air, at about room temperature, i.e. 22° to 30° C., for a period of about 2 to 10 days under aseptic conditions. The exact time period will, of course, vary depending on the concentration of bacteria in the liquid culture. The drying should continue until the bacteria-carrier mixture appears totally dried. The remaining moisture content of the dried mixture should be approximate the relative humidity of the environment.

The composition resulting after the completion of drying includes dried, dormant yet viable Rhizobium together with the porous granular carrier in a loose cake. The cake is readily friable to yield a clumped, coarsely granular product. This granular product may or may not be re-ground to a more powdery form depending on the particular delivery strategy to be used.

Thus, depending on the delivery procedure to be used, the bacteria-carrier mixture can then be ground to a relatively fine powder for use in dusting or coating directly on legume seeds with or without an adhesive or can be dusted on the field before or during planting. Alternatively coarser granuler bacteria-carrier mixture might not be ground, and then the dried granular mixture can be easily and directly introduced into the furrows during planting to inoculate the seeds. Thus the material produced from the drying of the bacteria-carrier mixture is readily adaptable to various delivery methods as may be desired for any given application.

A Rhizobium-inoculated leguminous seed coating prepared by the present invention would include a mixture of Rhizobium bacteria together with a porous, chemically inert carrier, wherein the bacteria-carrier mixture has been air-dried to a substantially moisture free state. The weight ratio of concentrated bacteria culture to dry carrier should be in the range of about 0.5 to 1.5, preferably about 1.0. Any of the Rhizobium species mentioned above can be used in this leguminous seed coating. The preferable carrier is selected from the group consisting of vermiculite, perlite, and charcoal. When charcoal is selected, the leguminous seed coating further includes a saccharide. The saccharide is introduced in a saturated solution to the bacterial suspension at a weight ratio of saccharide solution to bacterial suspension in the range of about 0.5–1.5, preferably about 1.0. Examples of suitable saccharides include sucrose, lactose, trehalose, sorbitol and adonital. It may be preferable to grind the dried bacteria-carrier mixture prior to coating the leguminous seed. If so, such grinding is preferably done after the mixture has been air-dried.

While this method is particularly useful for Rhizobium species for which presently recognized agriculture uses exist, it has also been found useful in drying viable cultures of other non-Rhizobium species, whether for agricultural or other applications.

The following non-limitative examples are intended to illustrate the present invention.

EXAMPLE 1

The bacteria used in this Example was a strain of Rhizobium japonicum, isolated from a soybean field in Louisiana. In each of the five experiments comprising Example 1, the bacteria was cultured for 14 days on AMA-agar. After culturing, the bacteria was harvested by scraping the culture from the agar support. The two carriers tested in this Example were perlite and charcoal. When perlite was used, the bacteria was first maintained at two different temperatures ($T_1$ and $T_2$) for a varying number of hours, and then mixed with the perlite carrier. When charcoal was selected as the carrier, the bacteria was first mixed with an equal weight of saturated sucrose and then maintained at the different temperatures ($T_1$ and $T_2$) for a varying number of hours. After the bacteria had been maintained for the required period of time, the bacteria was then mixed with an equal weight of charcoal. Table 1 illustrates the conditions for the five experiments which comprise Example 1. Table 2 contains the results of the experiment of Example 1, expressed as viable Rhizobium per gram dried product. The results illustrate the stability which can be achieved with the agricultural product of the present invention.

TABLE 1

| | | Conditions of Example 1 | | | |
|---|---|---|---|---|---|
| Experiment | culture | weight ratio, carrier/ bacteria | weight ratio, saccharide/ bacteria | hours at $T_1$ | hours at $T_2$ |
| (a) | 14 days, AMA-agar | 0.5 perlite | — | 4 hr, 23° C. | 18 hr, 10° C. |
| (b) | 14 days, AMA-agar | 1.0 perlite | — | 4 hr, 23° C. | 18 hr, 10° C. |
| (c) | 14 days, AMA-agar | 1.0 perlite | — | 18 hr, 23° C. | 7 hr, 10° C. |
| (d) | 14 days, AMA-agar | 1.0 charcoal | 1.0 sucrose | 4 hr, 23° C. | 18 hr, 10° C. |
| (e) | 14 days, AMA-agar | 1.0 charcoal | 1.0 sucrose | 18 hr, 23° C. | 7 hr, 10° C. |

TABLE 2

| | Results of Example 1 (viable Rhizobium per gram dried product) | | | | |
|---|---|---|---|---|---|
| Experiment | 1 week | 11 weeks | 13 weeks | 43 weeks | 48 weeks |
| (a) | $10^9$ | $10^9$ | | | $10^7$ |
| (b) | $10^9$ | $10^8$ | | | $10^8$ |
| (c) | $10^9$ | $10^9$ | $10^8$ | | |
| (d) | $10^9$ | $10^8$ | | | $10^6$ |
| (e) | $10^9$ | $10^9$ | $10^9$ | $10^8$ | |

EXAMPLE 2

In this Example, Rhizobium japonicum, isolated from a soybean field in Illinois, was tested. In the four experiments which comprise this Example, two different culture methods were used. In the first two experiments, the bacteria was cultured for 14 days on AMA-agar. In the second two experiments of this Example, the bacteria was cultured for 7 days on AMA-agar. As in Example 1, following harvesting of the bacteria, the bacteria was maintained at different temperatures for different periods of time prior to mixing with a carrier, the bacteria was first mixed with an equivalent weight of a saturated sucrose solution prior to maintaining the bacteria at $T_1$. The conditions used in Example 2 are illustrated in Table 3. The results of this Example are given in Table 4.

TABLE 3

| | | Conditions of Example 2 | | | |
|---|---|---|---|---|---|
| Experiment | culture | weight ratio, carrier/ bacteria | weight ratio, saccharide/ bacteria | hours at $T_1$ | hours at $T_2$ |
| (a) | 14 days, agar | 1.0 charcoal | 1.0 sucrose | 4 hr, 23° C. | 18 hr, 10° C. |
| (b) | 14 days, agar | 0.5 perlite | — | 4 hr, 23° C. | 18 hr, 10° C. |
| (c) | 7 days, agar | 1.0 perlite | — | 4 hr, 23° C. | 18 hr, 10° C. |
| (d) | 7 days, agar | 1.0 perlite | — | 22 hr, 23° C. | — |

TABLE 4

| | Results of Example 2 (viable Rhizobium per gram dried product) | | | | |
|---|---|---|---|---|---|
| Experiment | 1 week | 5 weeks | 11 weeks | 15 weeks | 48 weeks |
| (a) | $10^7$ | | $10^7$ | | |
| (b) | $10^{10}$ | | $10^{10}$ | | $10^6$ |
| (c) | $10^9$ | $5 \times 10^8$ | | | |
| (d) | $10^9$ | $5 \times 10^8$ | | $2 \times 10^8$ | |

EXAMPLE 3

In this Example, the bacteria a Rhizobium japonicum culture isolated from a field in Iowa was tested. The conditions of Example 3 are given in Table 5, and the results of Example 3 expressed in viable Rhizobium per gram dried product are given in Table 6.

TABLE 5

| | | Conditions of Example 3 | | | |
|---|---|---|---|---|---|
| Experiment | culture | weight ratio, carrier/ bacteria | weight ratio, saccharide/ bacteria | hours at $T_1$ | hours at $T_2$ |
| (a) | 14 days, agar | 1.0 perlite | — | 4 hr, 23° C. | 18 hr, 10° C. |
| (b) | 14 days, agar | 1.0 charcoal | 1.0 sucrose | 4 hr, 23° C. | 18 hr, 10° C. |
| (c) | 7 days, agar | 1.0 perlite | — | 24 hr, 23° C. | — |

TABLE 6

| | Results of Example 3 (viable Rhizobium per gram dried product) | | | | | |
|---|---|---|---|---|---|---|
| Experiment | 1 week | 5 weeks | 6 weeks | 9 weeks | 14 weeks | 18 weeks | 19 weeks |
| (a) | $10^{10}$ | $10^{10}$ | | | $10^9$ | | $10^7$ |
| (b) | $10^{10}$ | $10^8$ | | $10^6$ | | | |
| (c) | $10^{10}$ | | | $10^{10}$ | | $10^9$ | $10^7$ |

EXAMPLE 4

In this example, another Rhizobium japonicum isolated from Louisiana was tested. The conditions of Example 4 are given in Table 7, and the results of this Example are given in Table 8.

TABLE 7

| | | Conditions of Example 4 | | | |
|---|---|---|---|---|---|
| Experiment | culture | weight ratio, carrier/ bacteria | weight ratio, saccharide/ bacteria | hours at $T_1$ | hours at $T_2$ |
| (a) | 14 days, agar | 1.0 perlite | — | 4 hr, 23° C. | 18 hr, 10° C. |
| (b) | 14 days, agar | 1.0 charcoal | 1.0 sucrose | 4 hr, 23° C. | 18 hr, 10° C. |

TABLE 8

| | Results of Example 4 (viable Rhizobium per gram dried product) | | | | |
|---|---|---|---|---|---|
| Experiment | 1 week | 5 weeks | 9 weeks | 14 weeks | 19 weeks |
| (a) | $10^{10}$ | | $10^{10}$ | $10^8$ | $10^7$ |
| (b) | $10^{10}$ | $10^9$ | $10^9$ | $10^8$ | $10^7$ |

EXAMPLE 5

In this example, another Rhizobium japonicum isolate from Iowa was utilized. The conditions of Example 5 are expressed in Table 9. The results of this Example are given in Table 10.

TABLE 9

| | | Conditions of Example 5 | | | |
|---|---|---|---|---|---|
| Experiment | culture | weight ratio, carrier/ bacteria | weight ratio, saccharide/ bacteria | hours at $T_1$ | hours at $T_2$ |
| (a) | 14 days, | 1.0 | — | 4 hr, | 18 hr, |

TABLE 9-continued

| | Conditions of Example 5 | | | | |
|---|---|---|---|---|---|
| Experiment | culture | weight ratio, carrier/ bacteria | weight ratio, saccharide/ bacteria | hours at $T_1$ | hours at $T_2$ |
| (b) | agar 14 days, agar | perlite 1.0 charcoal | 1.0 sucrose | 23° C. 4 hr, 23° C. | 10° C. 18 hr, 10° C. |

TABLE 10

| | Results of Example 5 (viable Rhizobium per gram dried product) | | | | |
|---|---|---|---|---|---|
| Experiment | 1 week | 5 weeks | 9 weeks | 14 weeks | 19 weeks |
| (a) | $10^{10}$ | $10^{10}$ | $10^9$ | $10^8$ | $10^7$ |
| (b) | $10^8$ | $10^8$ | $10^7$ | | |

EXAMPLE 6

In this example, the same method was tested on two non-Rhizobium bacteria. Two bacterial cultures, designated LA1c-2 and LA1c-6, were isolated from the roots of soybean plants in the state of Louisiana. Neither culture will nodulate a legume, as does Rhizobium. Both cultures are bacillus shaped, LA1c-2 being a long bacillus while LA1c-6 is short, while Rhizobium is, of course, a short rod shape. Both cultures are gram positive (Rhizobium in gram negative) and both cultures grow well on nutrient broths and agars which do not favor Rhizobium cultures.

Using perlite as the granular carrier, dried mixtures of each of these cultures was prepared. The dried preparations were examined and found to contain $1.2 \times 10^9$ viable bacteria per gram for LA1c-2 and $1.9 \times 10^9$ viable bacteria per gram for LA1c-6. In each case approximately 5% of the bacteria were revived.

It is to be understood that modification of the abovedescribed method for making an agriculturally useful bacterial composition and the agricultural product described here is possible within the spirit of the present invention. For example it may be advantageous to add other constituents to the dried bacterial product of the present invention. Other agricultural products, such as dry or liquid fertilizer or herbicides or pesticides not injurious to the bacteria could be added to the mixture. While it is particularly useful, in addition, to use the dried bacterial composition disclosed here as a seed coating, it could also be applied in furrow, or re-wetted and sprayed, or applied in some other fashion. Thus the present invention should not be limited to the above-described specification, but should be interpreted in accordance with the following claims.

What is claimed is:

1. A method for making an agriculturally useful inoculant of a high concentration of dormant but viable Rhizobium bacteria, comprising the steps of:
   (a) maintaining a concentrated suspension of said bacteria, substantially separated from its culture medium, at a concentration in excess of $10^{10}$ bacteria per gram, at a temperature in the range of about 0°-30° C. for a period in the range of about 3-25 hours under aseptic conditions;
   (b) mixing the bacterial suspension with a porous chemically inert mineral, granular carrier consisting of Perlite such that the weight ratio of dry carrier to concentrated bacterial suspension is in the range of about 0.5 to 1.5; and
   (c) air drying the bacteria-carrier mixture without applying heat or mechanical agitation between 22° and 30° C. for a period of about 2-10 days under aseptic conditions.

2. The method of claim 1, further comprising the step of grinding the bacteria-carrier mixture to a powder.

3. A method for making an agriculturally useful inoculant including a high concentration of dormant bacteria, comprising the steps of:
   (a) maintaining a concentrated suspension of bacteria, in a minimum of liquid culture medium, at a concentration in excess of $10^{10}$ bacteria per gram, at a temperature in the range of about 22°-30° C. for a period in the range of about 3-25 hours under aseptic conditions;
   (b) further maintaining the bacterial suspension at a temperature in the range of about 0°-15° C. for a period in the range of about 3-20 hours under aseptic conditions;
   (c) mixing the concentrated bacterial suspension with a porous, chemically inert granular carrier consisting of perlite such that the weight ratio of dry carrier to concentrated bacterial suspension is in the range of about 0.5 to 1.5; and
   (d) air drying the bacteria-carrier mixture without applying heat or mechanical treatment for a period of about 2-10 days under aseptic conditions at about room temperature.

4. The method of claim 3, further comprising the step of grinding the bacteria-carrier mixture to a powder.

5. An inoculant for legume seeds, consisting essentially of a mixture of dry, dormant but viable Rhizobium bacteria together with a porous, chemically inert perlite carrier, wherein the bacteria-carrier mixture has been air-dried to a substantially moisture-free state and the weight ratio, pre-drying, of concentrated bacteria suspension to dry carrier is in the range of about 0.5-1.5, and the bacteria is present in the mixture at a density in excess of $10^9$ bacteria per gram.

6. The coating of claim 5, wherein the bacteria-carrier mixture has been ground to a powder.

7. An agriculturally useful composition comprising legume seeds coated with a coating consisting essentially of dried, dormant but viable Rhizobium bacteria mixed with a porous, chemically inert perlite carrier, wherein the bacteria-carrier mixture has been air-dried to a substantially moisture-free state and the weight ratio, pre-drying, of concentrated bacteria suspension to dry carrier is in the range of about 0.5 to 1.5, and the bacteria is present in the bacteria-carrier mixture at a density in excess of $10^9$ viable bacteria per gram.

* * * * *